United States Patent [19]
Koros et al.

[11] Patent Number: 6,113,534
[45] Date of Patent: Sep. 5, 2000

[54] ADJUSTABLE HEART SURFACE STABILIZER

[76] Inventors: Tibor B. Koros; Gabriel J. Koros, both of 610 Flinn Ave., Moorpark, Calif. 93021

[21] Appl. No.: 09/045,774

[22] Filed: Mar. 19, 1998

[51] Int. Cl.⁷ .................................................. A61B 17/00
[52] U.S. Cl. .......................................................... 600/213
[58] Field of Search .................................. 600/201, 210, 600/227, 228, 229, 231, 232, 235, 37, 233, 213; 606/1

[56] References Cited

U.S. PATENT DOCUMENTS

| | | | |
|---|---|---|---|
| 5,865,730 | 2/1999 | Fox et al. ................................ | 600/228 |
| 5,875,782 | 3/1999 | Ferrari et al. ........................... | 128/898 |
| 5,876,332 | 3/1999 | Looney ................................... | 600/227 |
| 5,894,843 | 4/1999 | Benetti et al. ....................... | 606/190 X |

FOREIGN PATENT DOCUMENTS

0791330 A2   8/1997   European Pat. Off. .

*Primary Examiner*—Jeffrey A. Smith
*Attorney, Agent, or Firm*—David O'Reilly

[57] ABSTRACT

This invention relates to a device for stabilizing a particular area of the heart surface tissue for performing an anastomosis. In one embodiment the invention is comprised of a rectangular flat plate frame stabilizer having a bottom gripping surface for pressing against the surface tissue of the heart and minimizing motion during a heart bypass operation. Opposite closed sides or ends of the rectangular flat plate stabilizer substantially occlude the vessel while the surgery is being performed. A gap or opening in a side of the stabilizer allows for removal after the operation is completed. Various methods are described for locking the position of the stabilizer once it is pressed firmly in position against surface tissue of the heart. In one embodiment a knurled cylindrical rail is mounted on the stabilizer and engages a socket in a rigid shaft. A locking mechanism is provided by a pin and a handle for locking the rail in the socket in the rigid shaft. Other embodiments include a ball and socket mechanism that allows a wide range of adjustments, a hinged end on the rectangular frame to allow the stabilizer to be closed when the surgical procedure is being performed and an embodiment that allows external adjustment of the rectangular flat plate frame stabilizing plate against heart surface tissue from outside the surgical site.

18 Claims, 11 Drawing Sheets

ADJUSTABLE HEART SURFACE STABILIZER

BACKGROUND OF THE INVENTION

1. Field of the Invention

This invention relates to surgical instruments for use in heart bypass surgery and more particularly relates to an adjustable heart surface stabilizer to stabilize a surgical site on heart surface tissue against the motion of the beating heart.

2. Background Information

Heart bypass surgery known as coronary artery bypass graft (CABG) procedure has become a widely used effective treatment for a heart ailment known as arteriosclerosis. This disease is a restriction "clogging" of blood to the heart muscle. This condition is treated by performing a coronary artery bypass graft procedure to bypass the clogged arteries. In some cases when there are blockages to several arteries double, triple, and quadruple bypass grafts have to be made. The grafts bypass the obstructed or occluded portion restoring normal life giving blood flow to the heart muscle. The graft is usually obtained from an artery or vein in another part of the body.

When surgeons initially began using this surgical technique heart bypass machines were used and the heart was temporarily stopped. This resulted in long surgical procedures necessary to hook the patient up to a heart bypass machine so their blood was circulated and oxygenated while surgery was being performed on the heart. This made the surgery long increasing the trauma to the patient and made the procedure risky to the patient's health.

When the grafts were completed the patient had to be removed from the heart bypass machine and the heart re-started. The risk to the patient to stop, bypass and re-start the heart was very great. Efforts have been made to improve the treatment to reduce the trauma to the patient. These efforts are directed to procedures that are less invasive and less traumatic but are techniques that still require the use of heart bypass (cardiopulmonary bypass) machines and stopping the heart (cardioplagia). The risk to the patient could be greatly reduced if the need to stop the heart could be avoided. Without the need to stop the heart the intensive surgical procedure of connecting the patient to a cardiopulmonary bypass machine would be eliminated.

New procedures have been developed to perform the heart bypass surgery without stopping the heart. In these procedures the heart is still beating while the surgery is being performed to attach a graft to the effected area. The surgery can be performed without the necessity to make a large incision down the center of the chest and cut through the entire sternum in order to connect the patient to a heart bypass machine. The surgery is thus much less invasive and can be performed through the smaller incisions between the ribs. A graft is sewn in to bypass an obstruction while the heart is still beating.

The grafting procedure known as "anastomosis" restores blood flow with a vein or arterial graft that "bypasses" a clogged or obstructed artery such as the left anterior descending artery or other vessel. Typically a bypass is grafted to a blood source that is unobstructed to bypass the occlude artery obstruction restoring blood flow to the heart muscle. In some cases several grafts are required to bypass two, three or more obstructions. This procedure is difficult with the heart beating. Ends of the graft must be carefully sewn to the arteries on either sides of the obstruction with delicate small sutures to firmly attach the graft to prevent any leaks.

Methods have been devised to stabilize the outer layer of the heart surface tissue with limited success. One method is to place sutures on opposite sides of the surgical site in the outer layer where the surgery is to be performed and stretch the tissue to minimize movement. The tissue is stretched tightly to minimize movement while the heart muscle continues to beat. This procedure presents some risk of temporary damage to the outer tissue involved. Also this procedure takes additional time and is less than ideal.

Another alternative is to use a suction device to stabilize the outer surface tissue of the heart where the surgery is to be performed. A suction device with several ports is attached to the heart outer surface tissue to reduce motion of the outer layer. This method while effective can cause bruising and temporary small hematomas at the site of e suction parts. There is a need for a surgical instrument that can effectively reduce motion and stabilize a localize small area of heart surface tissue where an anastomosis is to be performed. An instrument that can be quickly and easily installed would allow an anastomosis to be performed more effectively, more easily, more quickly, more safely with much less trauma to the patient.

A device for stabilizing an area of surface tissue of the heart is described in European Patent Application Number 97102789.1 published on Aug. 27, 1997. In this application numerous configuration and variation of planar members attached to shafts are described. A plethora of complicated shafts and mechanisms for mounting and manipulating the contrast members are shown as well as numerous design for the contact members.

It is one object of the present invention to provide a surgical instrument that can stabilize a localized surgical site on surface tissue of the heart for performing an anastomosis.

Another object of the present invention is to provide a surgical instrument comprised of a rectangular flat frame having sections that press against a heart surface tissue at a surgical site and minimize motion.

Yet another object of the present invention is to provide a flat stabilizing plate having gripping surfaces to firmly stabilize and cushion a surgical site and a heart surface tissue against heart beat motion.

Still another object of the present invention is to provide a simple, easy way manipulate a flat rectangular stabilizer that is adjustable to angles and conform to the shape of the heart.

Yet another object of the present invention is to provide a rectangular flat plate heart surface stabilizer that is simple in construction and easy to use.

Still another object of the invention is to provide a heart stabilizer attached to a rigid shaft that can be quickly and easily attached to a retractor.

Yet another object of the present invention is to provide a rectangular flat plate stabilizer having an adjustable locking connection to a rigid shaft for adjusting the angle of the stabilizer.

Still another object of the present invention is to provide a heart surface area stabilizer that can apply pressure to a blood vessel to reduce the flow of blood at the surgical site.

Another object of the present invention is to provide a rectangular flat plate stabilizer for occluding the flow of blood in a vessel during an anastomosis.

Still another object of the invention is to provide a rectangular flat plate stabilizer having a hinged side for removing the stabilizer after completion of an anastomosis.

Another object of the present invention is to provide a flat plate heart surface stabilizer adjustably connected to a rigid shaft having clamps means in said shaft for locking the position of the stabilizer after positioning and adjustment.

Still another object of the present invention is to provide a surgical instrument of a rectangular flat frame for stabilized surface tissue on the heart during heart surgery including an arrangement for adjusting the angle of the flat rectangular plate from outside the incision.

Yet another object of the present invention is to provide a heart surface tissue stabilizing device that is adjustable by means of a wobble plate mounted on the outer end of a shaft for making adjustments from outside the incision.

Still another object of the present invention is to provide a heart surface tissue stabilizing device of an adjustable flat rectangular plate having a gimbal or yoke arrangement for adjusting the position of the plate against the heart surface tissue from outside the incision.

BRIEF DESCRIPTION OF THE INVENTION

The purpose of the present invention is to provide a heart surface stabilizing device having an adjustable mechanism for adjusting the position of the stabilizer to conform to the surface area at the heart at the surgical site.

There are heart stabilizing devices in use comprised of a flat planar member for contacting the surface of the heart at a surgical site to stabilize the motion against the beating of the heart. The present invention seeks to improve on this principle by providing a device that is simple and easy to use and can be manipulated to adjust the angle of the stabilizer to the position or shape of the heart at the surgical site.

One embodiment of the invention is a flat rectangular frame having a slot in one side for removing the stabilizing device after a completion of an anastomosis. The rectangular frame has a surface constructed to grip the surface tissue of the heart and hold it firmly against the motion of the beating of the heart. The rectangular frame stabilizer is attached to a rigid shaft by a mechanism which allows the angle of the stabilizer to be adjusted to conform to the surgical site. In one embodiment the adjustable devices is in the form of a curved rail attached to the top of the rectangular framed stabilizer engaging a socket or channel in the end of the mounting shaft. A pin slidably inserted in the mounting shaft clamps the rail securely in the socket. Loosening the pin allows the rectangular frame stabilizer rail to be adjustably positioned in the socket to vary the angle of the stabilizer to conform to the surface area at the surgical site on the heart.

Various configurations are provided on the bottom surface on the rectangular frame stabilizer to improve the frictional grip on the surface tissue. In one of these embodiments a dimpled surface is provided to provide increasing friction. In another embodiment the surface is variegated similar to the tracks of a tire. Still another embodiment the undersurface of the rectangular framed stabilizer is cross-cut to provide a rough firm gripping on the surface. Still another embodiment the gripping surface is provided by parallel slots to provide an uneven contact surface. In still another embodiment the bottom of the rectangular flat stabilizer is provided with a resilient cushioning material such as a plastic forming a chamber that can be filled with a liquid or a gel to provide a soft cushioning surface.

Another alternative is to construct the rail for the adjustable stabilizer with only one end connected. This allows the rail to pass through a bore in the end of the shaft to be clamped by the pin. Preferably the pin has a semi-circular end that fits the contour of the mounting rail to provide a more positive locking action to hold the stabilizing member in the adjusted position. Further, the rail is preferably provided with a cross-cut knurled surface to increase the friction and provide positive locking without the need for a great amount of force.

In the embodiments with the adjustable rail, the stabilizer is first positioned at the surgical site with the stabilizer pressing on the surface area of the heart at the surgical site. A handle on the pin is then rotated to tighten the shaft to securely lock the stabilizer in the adjusted position.

Another alternate embodiment involves the use of a ball and socket for providing an adjustable stabilizer. The rectangular frame stabilizer has a flange that is attached to a ball for engaging a socket in the end of the mounting shaft. The ball is mounted by inserting it through a hole in the shaft and seating it in the socket. The rectangular frame stabilizer may then be positioned at a surgical site to hold the area firmly against the motion of the beating heart and the pin screwed down to securely clamp the ball locking the position of the stabilizer. Preferably the end of the pin has a concave recess matching the contour of the ball to provide a more positive lock with minimum force.

In still another embodiment the ball on the rectangular frame stabilizer is in the form of a half sphere having a central cavity. The ball is inserted through a hole in the shaft and engages the socket. The locking pin has an end shaped to conform to the cavity in the half-sphere ball to securely clamp and lock the stabilizer into position.

Preferably the stabilizer is constructed to occlude the flow of blood in the vessel where the graft is being made. Thus, in one embodiment the stabilizer is a closed rectangular frame having one end hinged when the surgical procedure is complete so the stabilizer may be removed. The stabilizer has sides that are pressed firmly on a surface vessel on opposite sides where an incision is to be made to occlude blood flow and reduce bleeding. In this embodiment the flat rectangular frame stabilizer is adjustably connected to a shaft with either of the methods such as the ball or half ball and socket previously described. The free end of the rectangular frame stabilizer is closed but is provided with a hinge to provide a gate for opening when the stabilizer is removed after completion of the surgery.

In another embodiment of the invention the stabilizer is comprised of a flat plate having a boss for attaching the stabilizer to a shaft. In this embodiment the shaft is secured to the stabilizer by a conical pin passing through an eyelet on the end of the clamping pin. Both the boss and the conical head on the pin allow for a wide range of adjustments for the stabilizing device.

Two additional embodiments provide adjustment of the stabilizing flat rectangular plate from outside the incision. In both embodiments the flat rectangular plate stabilizer is adjustably attached to the end of the shaft. In one embodiment the flat rectangular stabilizer is adjusted by a wobble plate mounted on a ball and connected to the stabilizing plate by cables. The wobble plate at the top of the shaft adjusts the flat rectangular stabilizing plate by tilting the wobble plate on the spherical ball. In this embodiment the stabilizer may be positioned in the incision and pressed against the heart surface tissue where there is an occluded artery. The position is then adjusted to the heart contour by tilting the wobble plate to move the heart stabilizing flat rectangular plate up or down or side to side until it is in proper position against surface tissue of the heart. The position of the stabilizing plate is then fixed by tightening a rod passing through the stabilizer shaft.

In another embodiment adjustment from outside the incision is provided by a gimbal arrangement comprised of coaxial yokes mounted on the exterior or distal end of the stabilizer shaft connected to the adjustable flat rectangular plate by cables. In this embodiment the position of the flat rectangular plate after placement against the heart tissue is adjusted by tilting the coaxial yoke from side to side or forward or back until the position of the flat rectangular plate matches the contour of the heart at the occluded artery.

In each of the embodiments described above the stabilizing device can be constructed of surgical steel or a rigid disposable synthetic disposable material if desired. The synthetic material allows the stabilizer to be removed from the shaft for disposal after use in the surgical procedure.

Other objects, advantages and novel features of the invention will become apparent from the following detailed description when considered in conjunction with accompanying drawings wherein like reference numbers identify like parts throughout.

DETAILED DESCRIPTION OF THE INVENTION

This invention is for an improvement in a stabilizing device for use in heart bypass surgery or anastomosis. The stabilizing device as previously conceived apply damping or stabilizing pressure to the surgical site on a surface area of the heart. The purpose of the device is to minimize movement of the surface tissue of the heart so that a graft can be attached to bypass an obstructed vessel. This device substantially reduces the trauma to the patient by allowing the operation to be complete in much less time without the need to connect the patient to a cardiopulmonary bypass machine.

A heart surface stabilizing device 10 is illustrated in FIGS. 1 through 4. The heart stabilizing device is comprised of a rectangular flat frame 12 having a slot or opening 14 on one side to allow the device to be removed after completion of the surgical procedure. Preferably rectangular flat frame 12 is constructed of surgical steel but it may also be manufactured of a rigid synthetic material to be disposable. Rigid rectangular frame 12 is connected to a rigid shaft 16 by means of a curved rail 18 attached to the upper surface of the rectangular flat frame 12. Rail 18 engages a socket 20 on the end of rigid shaft 16. Rail 18 is securely clamped in socket 20 by applying pressure through knob or handle 22 compressing and clamping rod 24 against rail 18. Shaft 16 can be secured to a retractor frame 26 by any suitable means.

Figures 1, 7, 8:
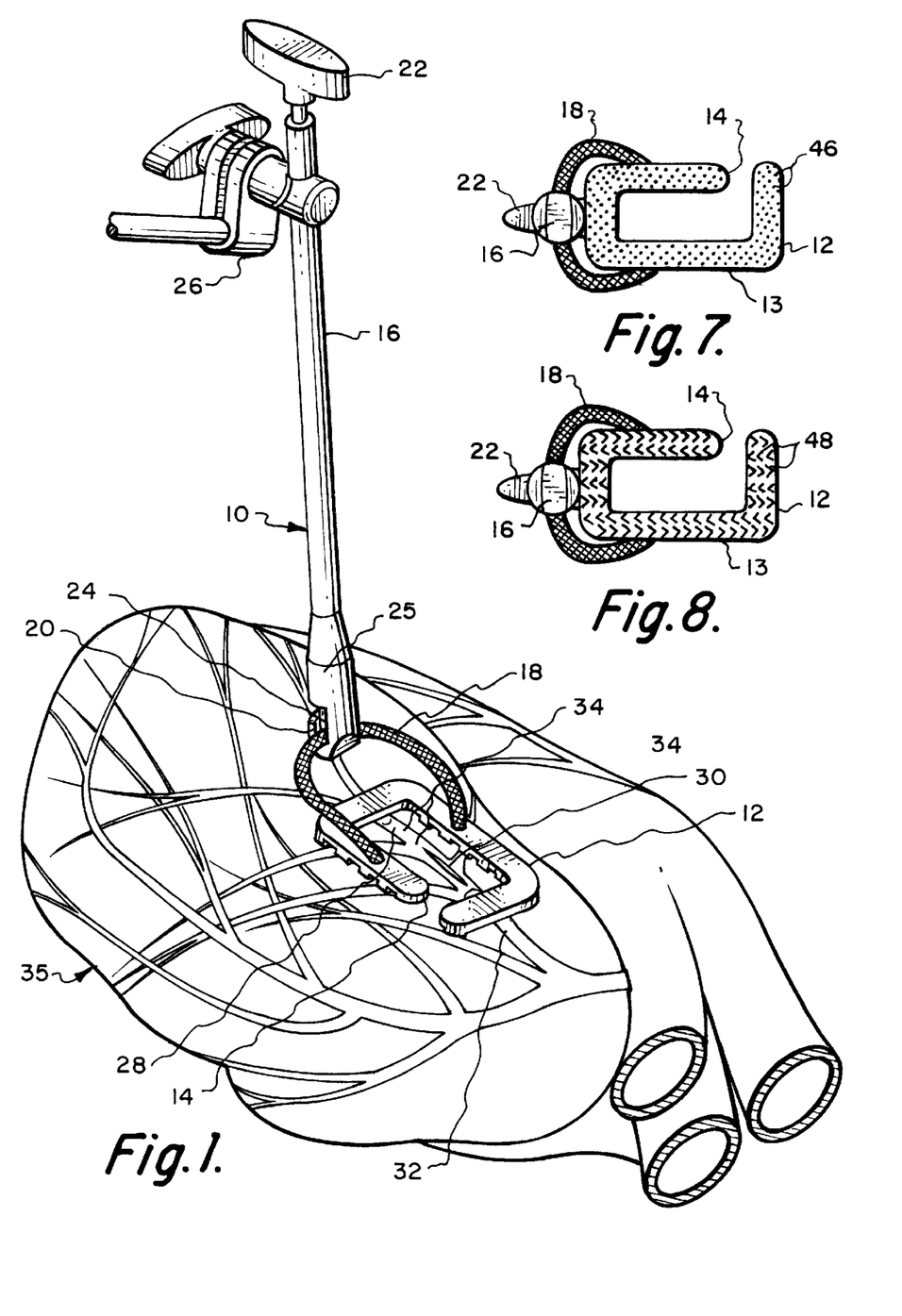
FIG. 1 illustrates one embodiment of the rectangular frame stabilizing device applying pressure to a surface tissue of a heart during an anastomosis.
FIG. 7 is another bottom view of the stabilizing device illustrating yet another method of improving the gripping surface of the stabilizer.
FIG. 8 is still another view of the bottom of the stabilizing device illustrating a surface construction to increase the gripping force.

Stabilizing rectangular flat frame 12 allows pressure and compression of a vessel 28 for attachment of a graft to an incision 30 in the vessel. Closed ends 32 and 34 apply pressure to vessel 28 on opposite sides of incision 30 to substantially occlude the flow of blood minimizing blood loss.

Figures 2, 9, 10:
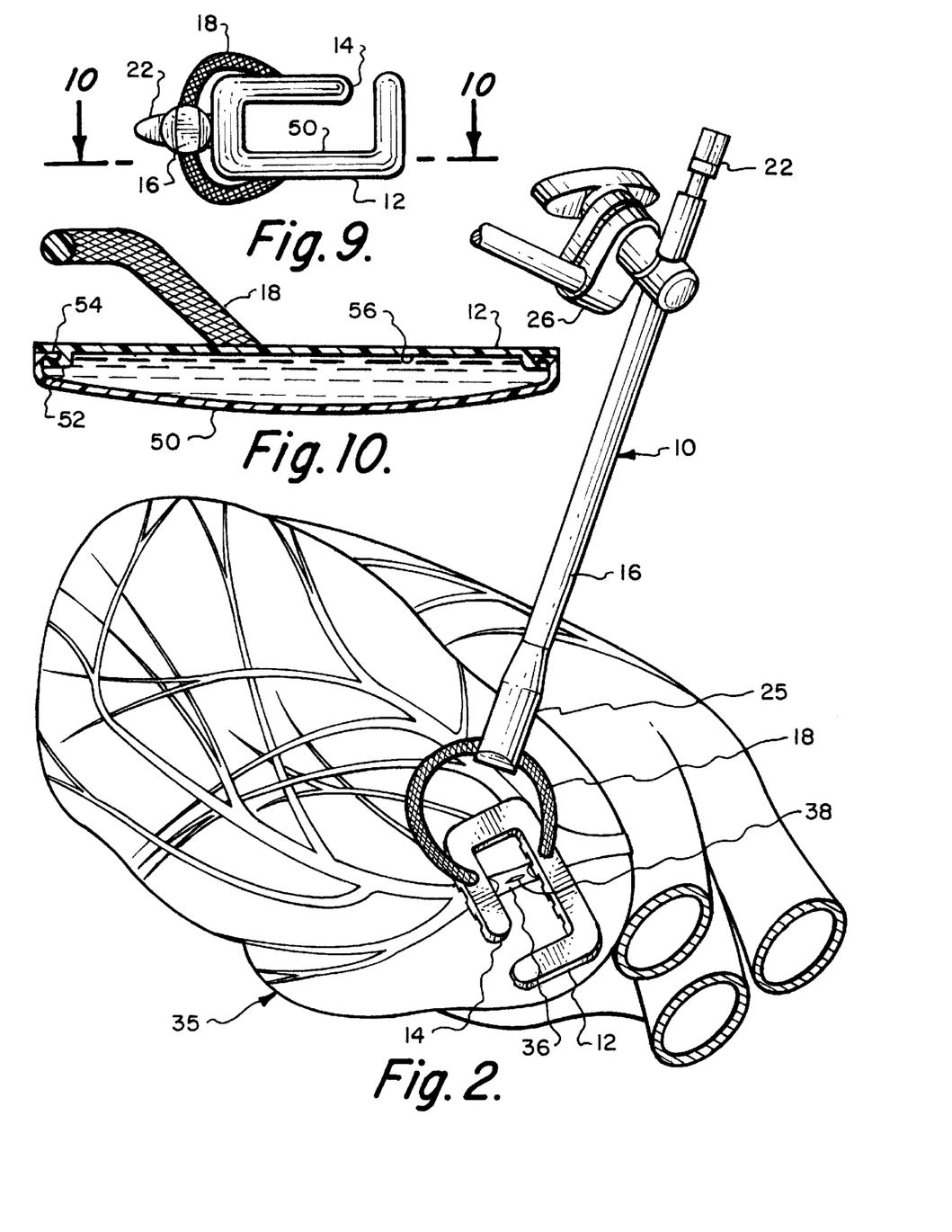
FIG. 2 illustrates the embodiment of FIG. 1 and its wide range of adjustable positions for performing an anastomosis.
FIG. 9 is a bottom view of a stabilizing device having a resilient soft cushioning surface.
FIG. 10 is a sectional view taken at 10—10 of FIG. 9.
Figures 3, 4, 5, 6:
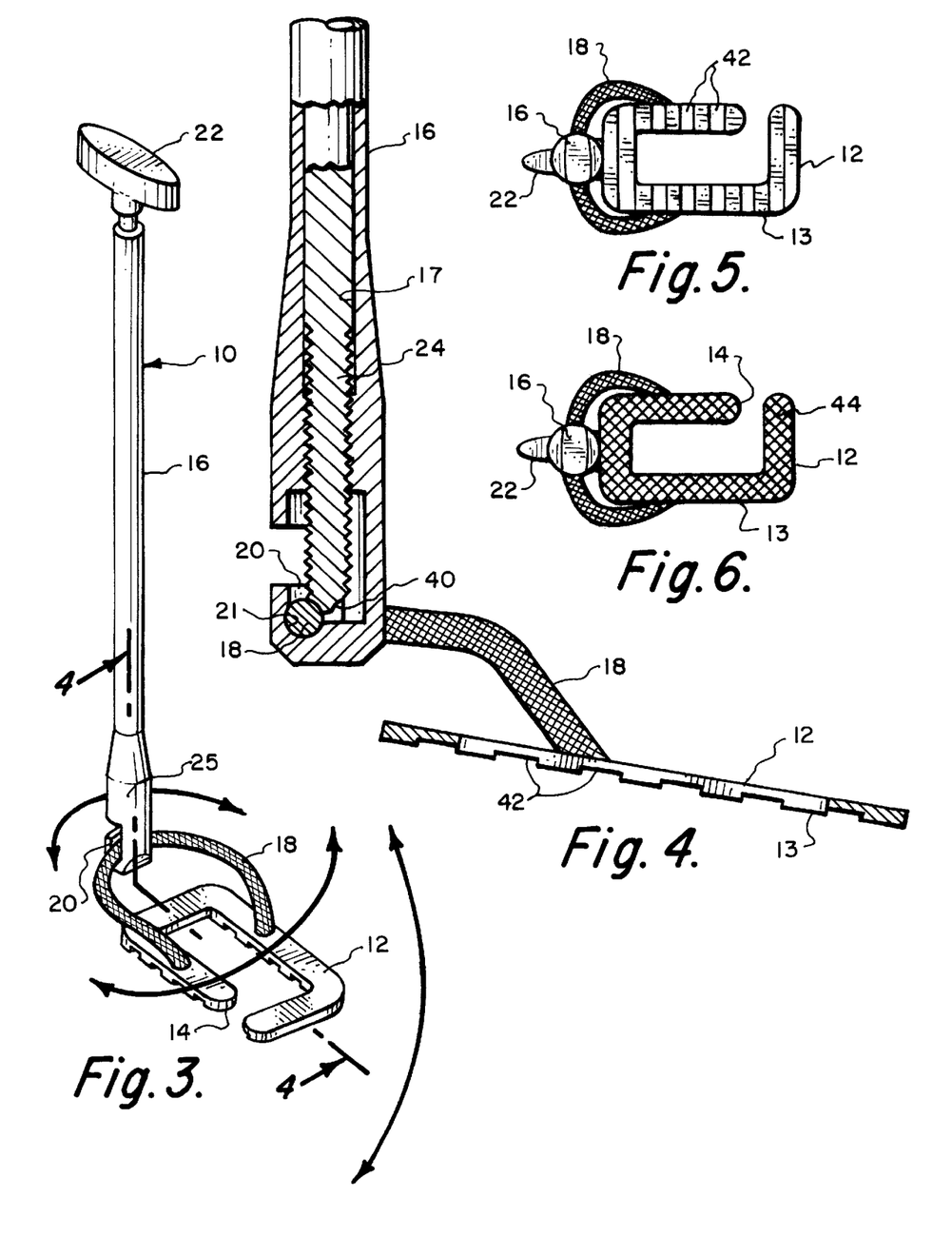
FIG. 3 illustrates the mounting on the rectangular frame stabilizing device to a shaft and the wide variety of adjustments available.
FIG. 4 is a partial sectional view taken at 4—4 of FIG. 3.
FIG. 5 is a bottom view of the stabilizing device of FIGS. 1 through 4 illustrating a construction to improve the gripping surface of the stabilizer.
FIG. 6 is a bottom view of the stabilizing device similar to FIG. 5 illustrating another method of improving the gripping surface.

The construction and arrangement of rail 18 and its attachment to rigid shaft 16 allows placement at a wide variety of angles and positions as shown in FIG. 2. For example for a vessel 36 on the side of heart 35 rectangular flat stabilizer 12 can be adjusted by rotating and sliding rail 18 in socket 20 of the end 25 of shaft 16. Once the proper angle and position is required pressure is applied to vessel 36 on either side where incision 38 is to be made to substantially occlude blood flow. The position of rectangular flat frame stabilizer 12 is locked by rotating knob 22 to clamp pin 24 against rail 18. With the construction and arrangement as shown in FIG. 3 rectangular frame stabilizer 12 can be adjusted right or left, up or down as well as a wide range of angular positions by sliding rail 18 in socket 20. Flat rectangular stabilizer 12 could be positioned anywhere from right angles to rigid shaft 16 to positions almost at 180° with gripping surface upside down.

The connection of flat rectangular stabilizer 12 to rigid shaft 16 is illustrated in greater detail in sectional view of FIG. 4. Rail 18 is securely attached to upper surface of rectangular frame stabilizer 12 which has a lower surface 13 constructed to improve gripping force against the surface tissue of the heart as will be described in greater detail hereinafter. Rail 18 passes through socket 20 which preferably has a concave recess 21 conforming to the cylindrical shape of rail 18. Threaded end of pin 24 passing through bore 17 in shaft 16 engages rail 18 and is clamped by applying force through handle 22. Preferably end 40 of threaded rod 24 has a concave annulus 40 having a curvature shaped to fit the shape of the cylindrical rail 18 to provide a firm locking action when rod 24 is screwed tightly down with handle 22. Additionally cylindrical rail has a cross-cut knurled surface to increase the frictional force and improve locking by rod 24.

In addition the bottom surface 13 of stabilizer 12 can be provided with a variety of textures to improve the gripping and holding force applied to the surface tissue of the heart. The rectangular flat stabilizer 12 shown in FIGS. 4 and 5 is provided with a surface 13 having a plurality of parallel grooves 42 to improve the gripping surface. In the embodiment shown in FIG. 6 stabilizer 12 has a bottom surface 13 comprised of cross-cut serrations 44 providing a very rough surface to firmly hold the heart tissue. FIG. 7 shows yet another embodiment of stabilizer 12 having a plurality of dimples 46 on surface 13 providing an improved gripping force. And still another surface is provided by "tire track" or V-groove treads 48 cut into the surface.

Figures 11, 12, 13:
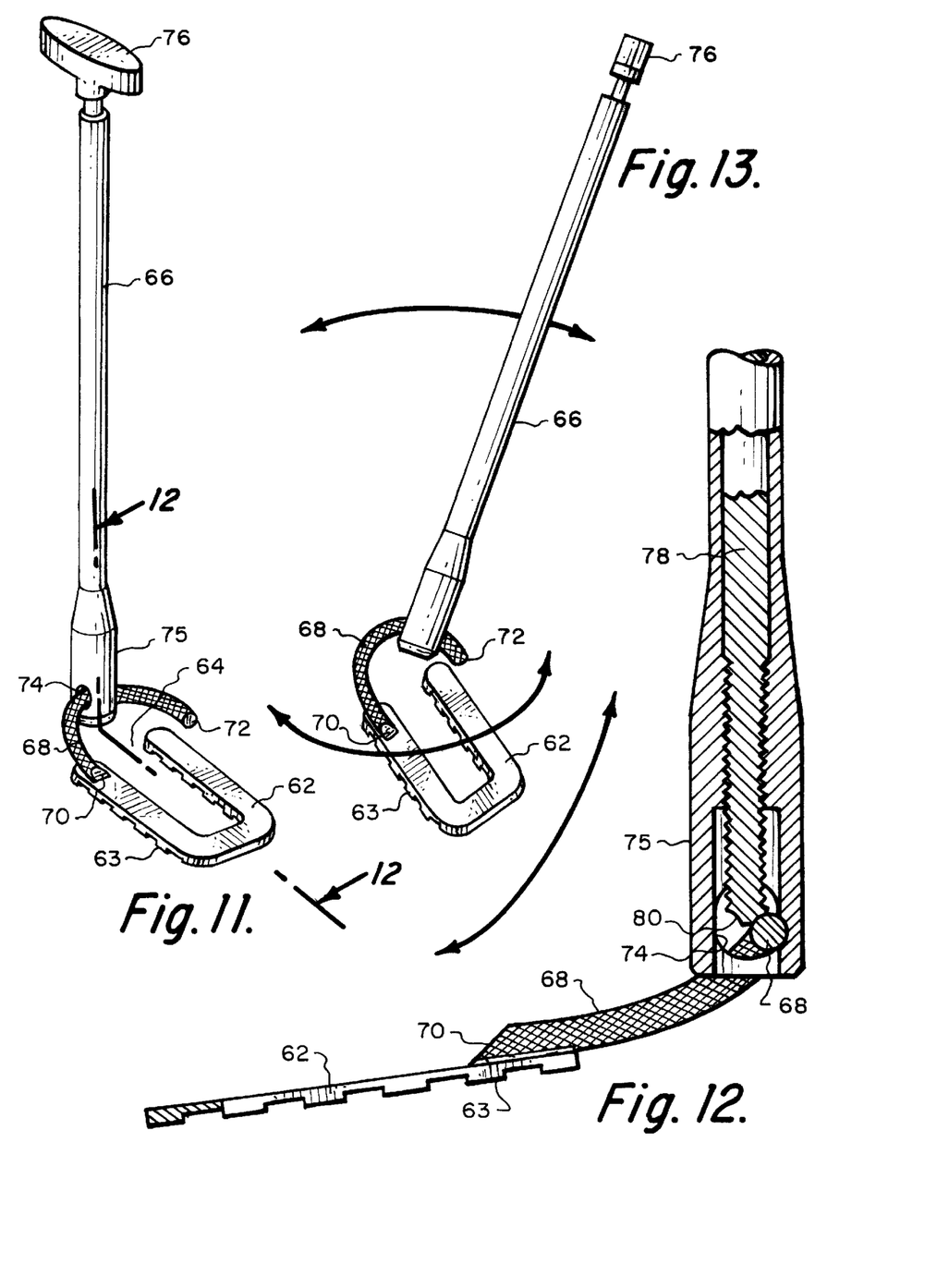
FIG. 11 is a isometric view of another embodiment of a rectangular frame stabilizing device.
FIG. 12 is a partial sectional view taken at 12—12 of FIG. 11.
FIG. 13 is an isometric view illustrating the wide variety of angular adjustments of the stabilizing device of FIG. 11.

Another embodiment to provide an improved gripping surface is shown in the bottom view of FIG. 9 and sectional view of FIG. 10. This embodiment provides a cushioning surface comprised of a flexible synthetic material 50 attached to stabilizer 12 around the peripheral slot 52 being engaged by a flange 54 on flexible material 50. When flexible synthetic material 50 is attached to stabilizer 12 a cavity 56 is provided which can be filled with any suitable pliable material such as a gel or a flue A variation of the embodiment in FIGS. 1 thorough 4 is illustrated in FIGS. 11 through 13. In this embodiment a stabilizer 62 is substantially rectangular with an opening at the rear end 64. Stabilizer 62 is attached to a rail 68 only at one end 70. Rail 68 curves upward and toward the opposite side of stabilizer 62 from fixed end 70 terminating in free end 72. Thus rail 68 has a non-linear curvature allowing a wide range of sideways and up and down adjustments of stabilizer 62.

This design also allows rail to be attached to rigid shaft 66 by passing through a bore 74 in end 75 on the rigid shaft 66. Rectangular flat stabilizer 62 has a bottom surface 63 having a plurality of cut grooves as shown in the embodiment of FIG. 5. However the bottom surface 63 of the embodiment of FIGS. 11 through 13 could have any one of the configurations illustrated in FIGS. 6 through 10.

With the open-ended construction of rail 68 shown in the embodiment of FIGS. 11 through 13 stabilizer 62 can be adjusted to a wide variety of positions from side to side or front to back as illustrated in FIG. 13. Flat rectangular stabilizer can thus be positioned on the surgical site of the heart at almost any angle and then locked in position by tightening down handle 76. Tightening handle 76 tightens rod 78 having concave angular groove 80 against the surface of cylindrical rail 68.

Figures 14, 15, 15A, 16:
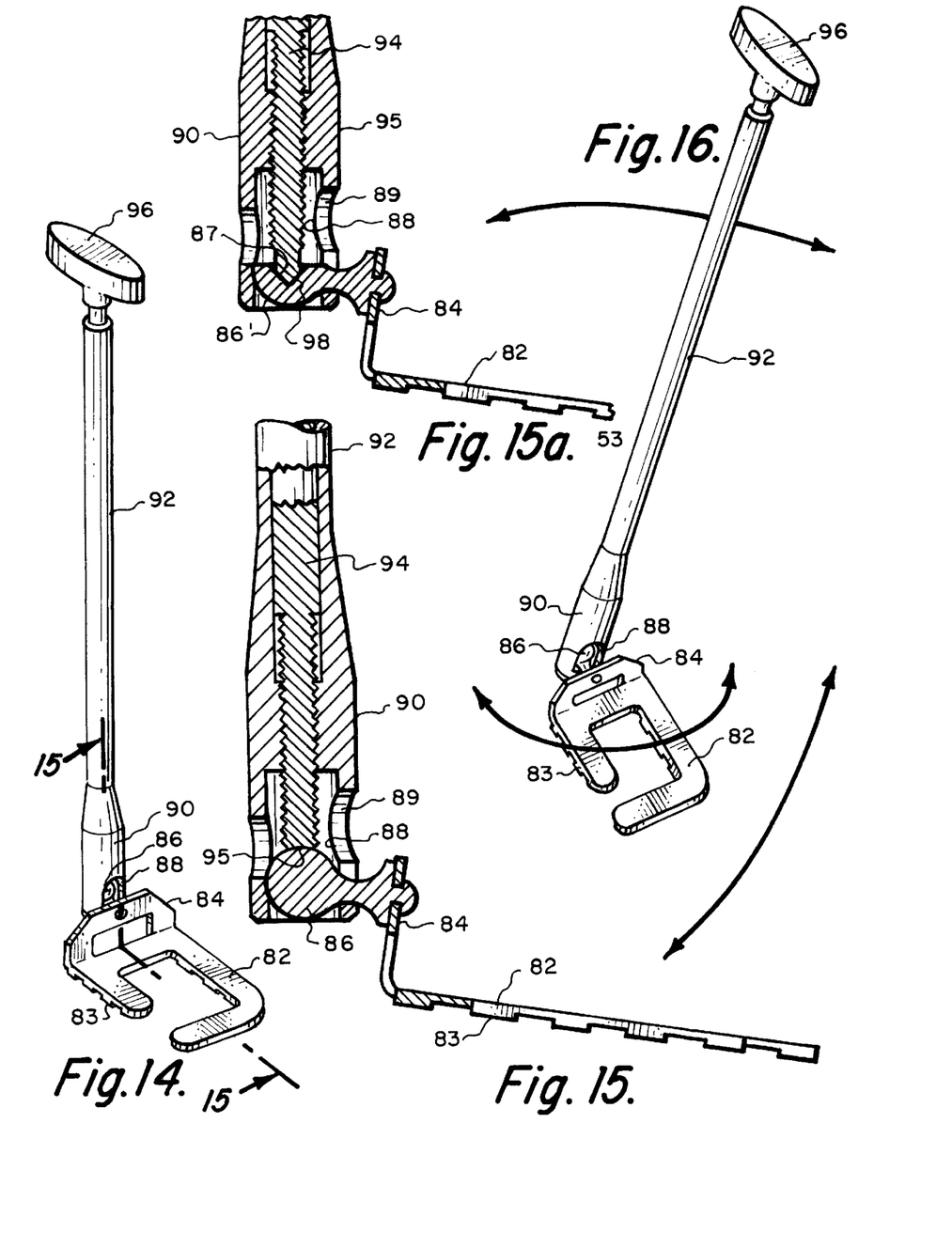
FIG. 14 is an isometric view of a stabilizing device having a ball and socket connection.
FIG. 15 is a partial sectional view taken at 15—15 of FIG. 14.
FIG. 15A is a partial sectional view similar to FIG. 15 showing an alternate ball and socket construction.
FIG. 16 is an isometric view of the embodiment of FIG. 14 showing the angular adjustment of the stabilizing device.

Another embodiment is illustrated in FIGS. 14 through 16. The purpose of these various embodiment is to provide a wide variety of adjustment angles for stabilizing a small surface area in the heart where an anastomosis is to be performed. As shown in FIG. 14 that rectangular stabilizer 82 has a vertical flange 84 securely attached to a ball 86 fitting socket 88 in end 90 of rigid shaft 92. Socket 88 is accessed through hole 89 in end 90. The position of flat rectangular stabilizer 82 is locked by means of a locking rod 94 inside rigid shaft 92 that is screwed down by handle 96. In this as well as other embodiments rectangular flat plate stabilizer 82 can be disposable. Stabilizer 82 can be easily removed from rigid shaft 92 by loosening rod 94 and slipping ball 86 out of socket 88 as before the bottom side 83 of stabilizer 82 can be made with any of the gripping configurations illustrated in FIGS. 5 through 10.

As shown in FIG. 16 the configuration of embodiments as shown in FIGS. 14 through 16 can be easily adjusted by rotating ball 86 in socket 88. Thus by rotating ball 86 in socket 88 flat rectangular stabilizer 82 can be moved from side to side or up and down or tilted to whatever angle is required. Stabilizer 82 is firmly placed on the surface of the area tissue on the heart where the anastomosis is required and locked in place by tightening end 95 of rod 94 with nob 96.

A variation of the embodiment of FIGS. 14 through 16 is illustrated in FIG. 15A. Instead of ball 86 a half-spherical ball 86' is provided having a socket 87 for receiving convex 98 on rod 94. As before half-spherical ball 86' is slipped through hole 89 in end 90 of rigid shaft 92 and seated in socket 88. Rod 94 then locks rectangular flat stabilizer 82 in place by engaging concave cavity 87 in half-spherical ball 86'.

Figures 17, 18, 18A, 19:
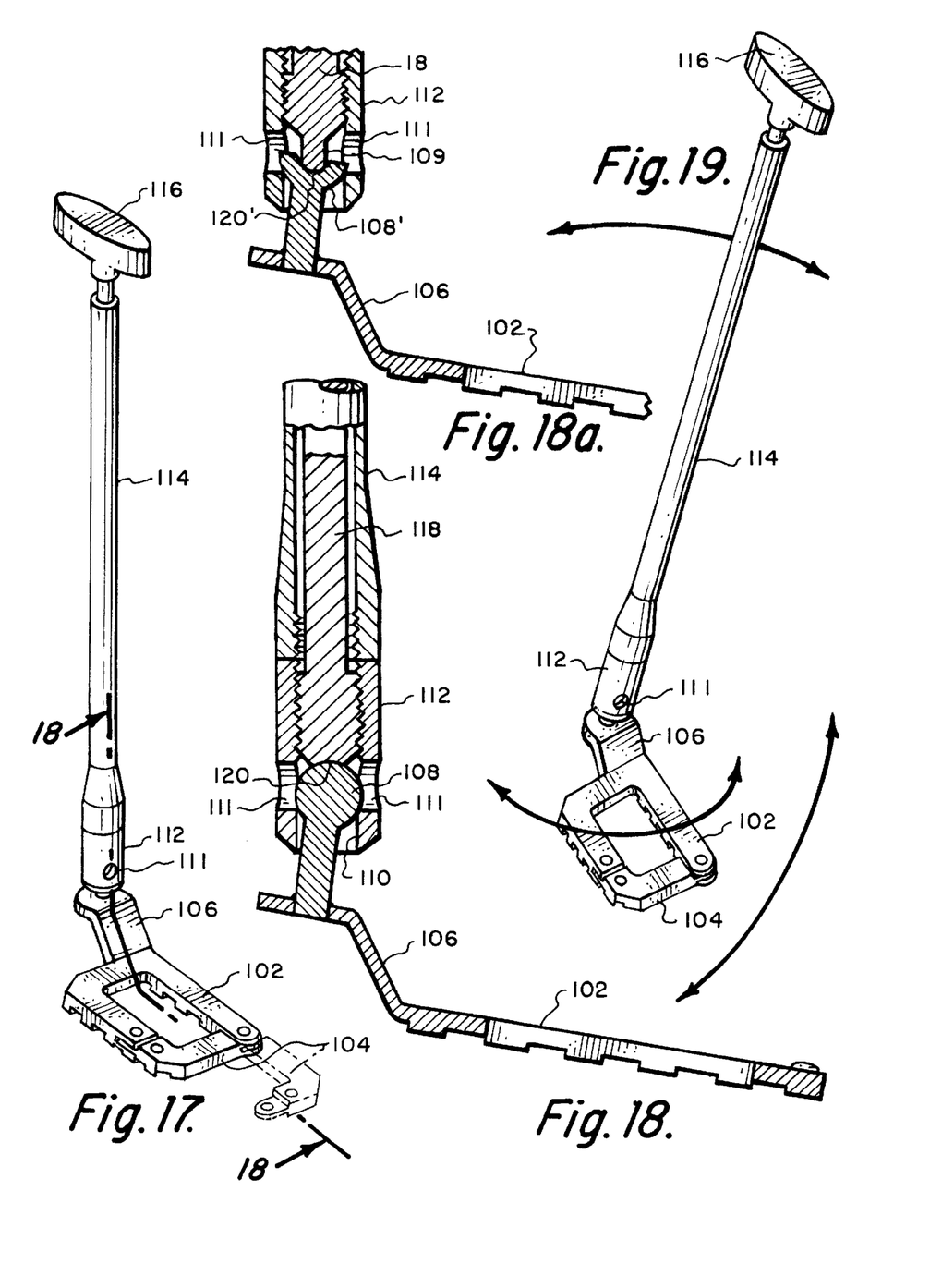
FIG. 17 is an isometric view of a rectangular frame stabilizing device having a hinged end for opening the device after completion of a surgical procedure.
FIG. 18 is a partial sectional view taken at 18—18 of FIG. 17.
FIG. 18A is a partial sectional view similar to FIG. 18 illustrating an alternate embodiment.
FIG. 19 is a view illustrating the adjustability of the embodiment of FIG. 17.

In the embodiment of FIGS. 17 through 19 a rectangular frame stabilizer 102 is provided having a hinged end 104 to allow the stabilizer to be open and closed for removal after the completion of the surgery. In this embodiment rectangular flat plate stabilizing 102 is connected by a flange 106 to a ball 108 in a socket 110 in end 112 of rigid shaft 114. Head member 112 on rigid shaft 114 is detachable so that stabilizer 102 and head member can be disposable.

As shown in FIG. 19 rectangular frame stabilizer 102 is rotatable 360° around rigid shaft 114 and tiltable from side to side and up and down. The position of rigid stabilizing frame 102 is locked by tightening nob 116 to clamp end 120 of rod 118 against ball 108. Holes or bores 111 in head end 112 of rigid shaft 114 allow ball 108 and thus rectangular frame stabilizer 102 to freely move in a wide variety of adjustable positions.

An optional variation of the embodiment of FIGS. 7 through 19 is illustrated in FIG. 18a. In this embodiment ball 108 is replaced with a half-spherical ball 108' having a cavity 109 to receiving the convex tip 120' of rod 118. Convex tip 120' is contoured to fit cavity 109 in half-spherical ball 108' to lock rectangular frame stabilizer in a preset position.

FIGS. 20 through 24 illustrated an embodiment in which a flat plate stabilizer 122 is offset from the rigid shaft 124. Rigid shaft 124 has a tubular head end 126 attached to flat plate stabilizer 122 by rod 128 having ring or eyelet 130. A conical, flat head screw 132 passes through eyelet 130 into slot 134 on boss 136 engaging threaded hole 138 in pin 140. Angled surfaces on boss 136 and conical head on screw 132 provide opposing locking surfaces as will be described in greater detail hereinafter.

Figures 20, 24:
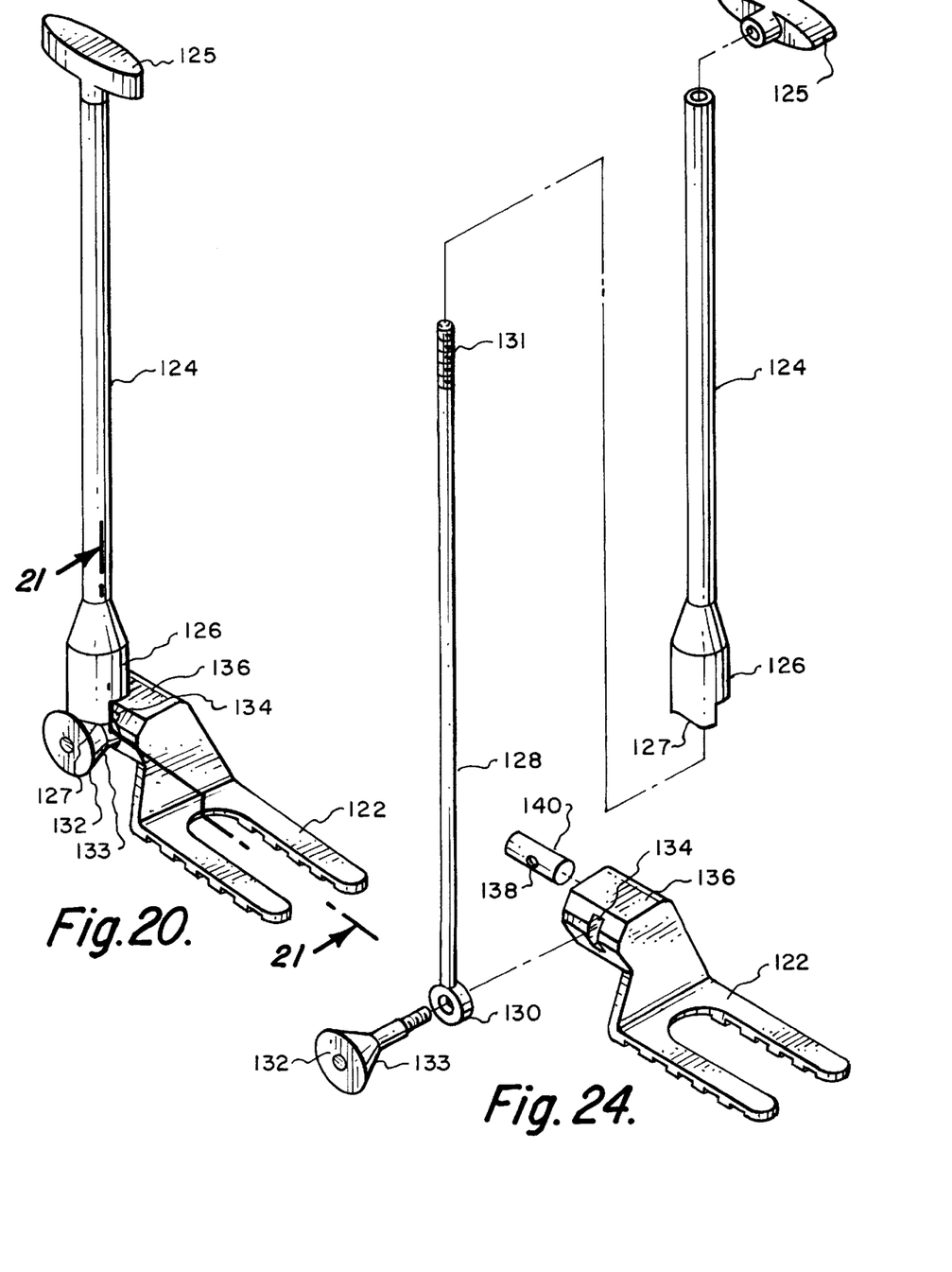
FIG. 20 is an isometric view of another stabilizing device with an alternate method of connecting the stabilizing device to a rigid shaft.
FIG. 24 is an exploded view illustrating the construction and assembly of the device of FIG. 20.

This embodiment is assembled as shown in FIG. 24 by passing screw 132 through ring or eyelet 130 on rod 128 into slot 134 and threading it into threaded hole 138 in pin 140. Rod 128 is then passed through bore 129 in shaft 124. Handle 125 is then threaded on threads 131 on rod 128. This construction and arrangement allows flat plate stabilizer 122 to rotate freely up and down rotate in a plane from side to side with shaft 124 being positioned as necessary and fastened to a retractor frame. The embodiment on FIGS. 20 through 24 is positioned with the flat plate stabilizer 122 pressing on surface tissue of the heart where an anastomosis is to be performed. The position is then locked by rotating handle 125 drawing rod 128 into bore 129 of shaft 124. This draws conical head 133 and angled surfaces on boss 130 (FIG. 22) up against an oblique angled surface 127 and on head end 126 of shaft 124 firmly locking the position of flat plate stabilizer 122.

Figures 21, 22, 23:
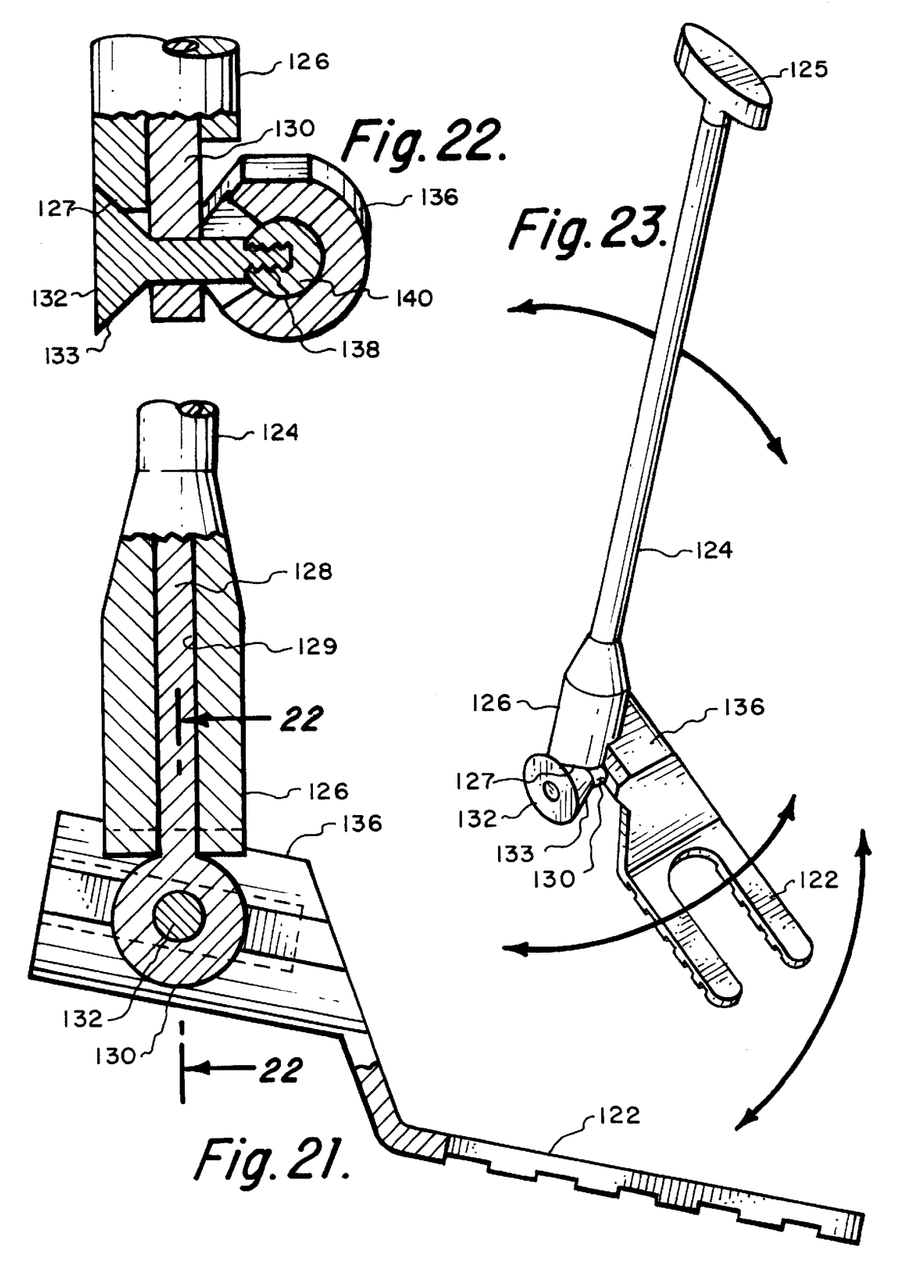
FIG. 21 is a partial sectional view taken at 21—21 of FIG. 20.
FIG. 22 is a partial sectional view taken at 22—22 of FIG. 21.
FIG. 23 is an isometric view illustrating the adjustability of the device of FIG. 20.

When assembled as shown in FIG. 23 flat plate stabilizer 122 can freely move in a vertical direction and rotate in a horizontal position for position on the surface tissue of the heart. The position is then locked by tightening handle 125 drawing rod 128 into shaft 124 forcing head in 126 firmly down against opposing conical surfaces of head 133 on screw 132 and similar angled surfaces on boss 134. Adjustments can be made by loosening handle 125 releasing clamping force of oblique surface 127 on conical surface 133 of screw 132. This will then again allow flat plate stabilizer 122 to be freely moved vertically or horizontally for positioning onto a heart vessel to perform an anastomosis.

Optional embodiments that allow for external adjustments of the heart stabilizing plate are illustrated in FIGS. 25 through 34. In the embodiment on FIGS. 25 through 29 heart stabilizing plate 142 is mounted on end 144 of shaft 146 in a manner similar to that shown in the embodiment of FIGS. 17 and 18. Barrel shaped end 144 has a socket 148 for receiving a ball 150 attached to stabilizing plate 142. This allows stabilizing plate 142 to be moved up or down or side to side to adjust it to the contour of the surface tissue of the heart.

Since on the purposes of these devices is to minimize trauma to the patient it is also important to keep the incision as small as possible. Therefore, it is an advantage if the heart stabilizing device can be manipulated and adjusted from outside the incision. Thus the embodiment of FIGS. 25 through 34 are conceived to provide such external adjustments.

Figures 25, 26:
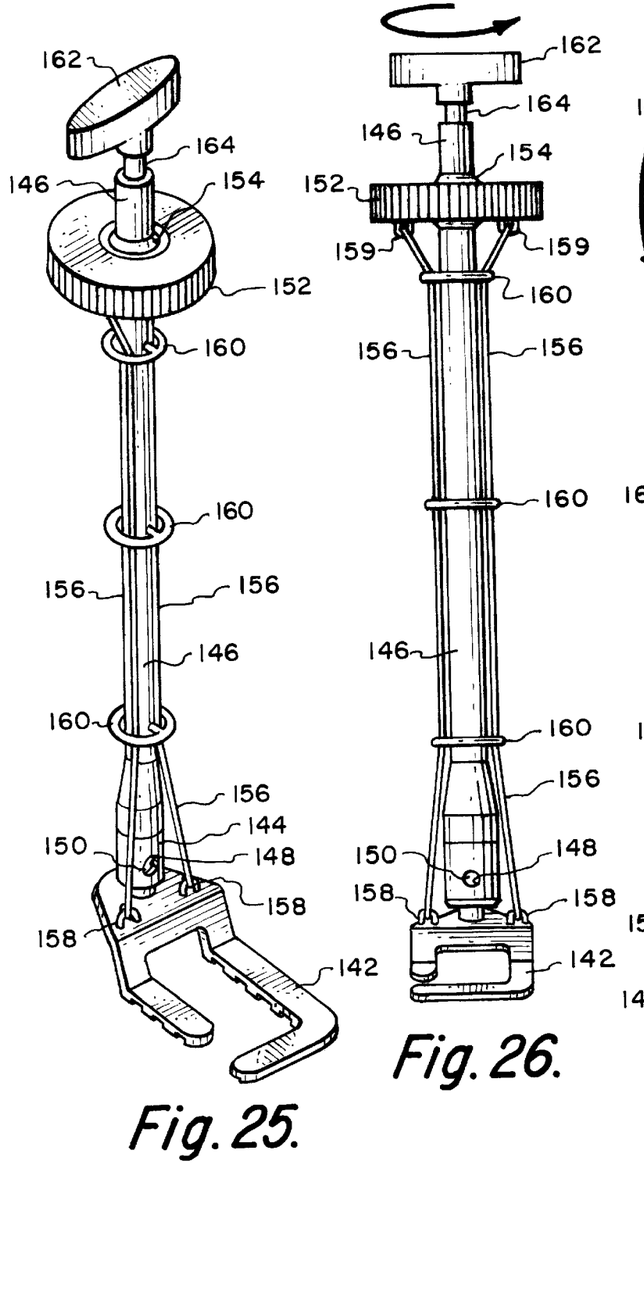
FIG. 25 is an isometric view of a heart surface tissue stabilizing device having a mechanism for externally adjusting the position of the heart stabilizing plate.
FIG. 26 is a front view of the embodiment of FIG. 25.
Figure 27:
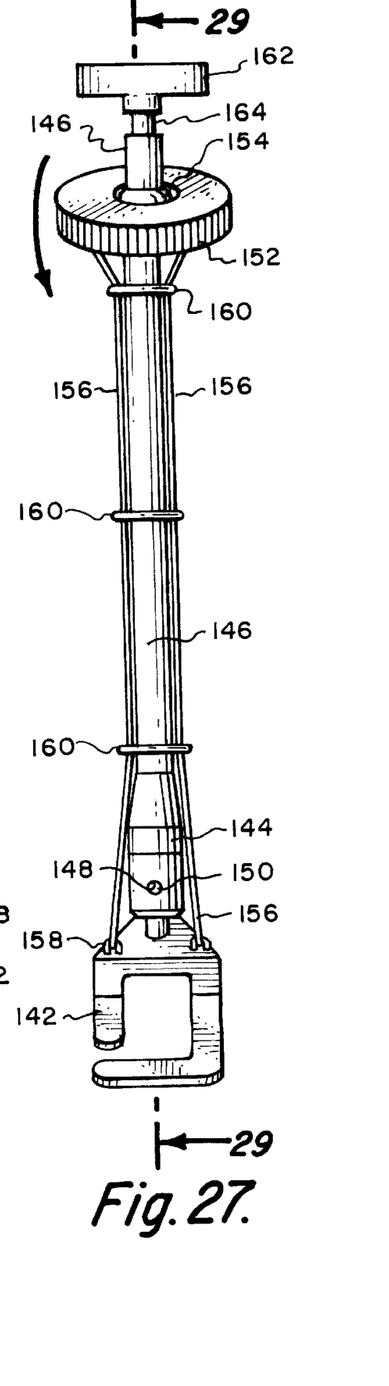
FIG. 27 is another front view of the heart stabilizing device of FIG. 25 illustrating adjustment of the heart stabilizing plate.

In the embodiment of FIG. 25, stabilizing plate 142 is adjusted by a wobble plate 152 mounted on a spherical ball 154 on the upper or distal end of shaft 146. Wobble plate 152 can be adjusted by tilting at any angle or direction forward, backward, or side to side. Wobble plate 152 is connected to stabilizing plate 142 by cables 156 which are attached to stabilizing plate 142 by annulets 158. Lanyards or cables 156 are restrained and guided by rings 160. The upper end of lanyards 156 are connected to wobble plate 152 also by annulets 159. After adjusting the position of stabilizing plate 142 against the heart tissue the position is locked as before by rotating handle 162 clamping rod 164 against ball 150 attached to stabilizing plate 142 as before.

Figures 28, 29:
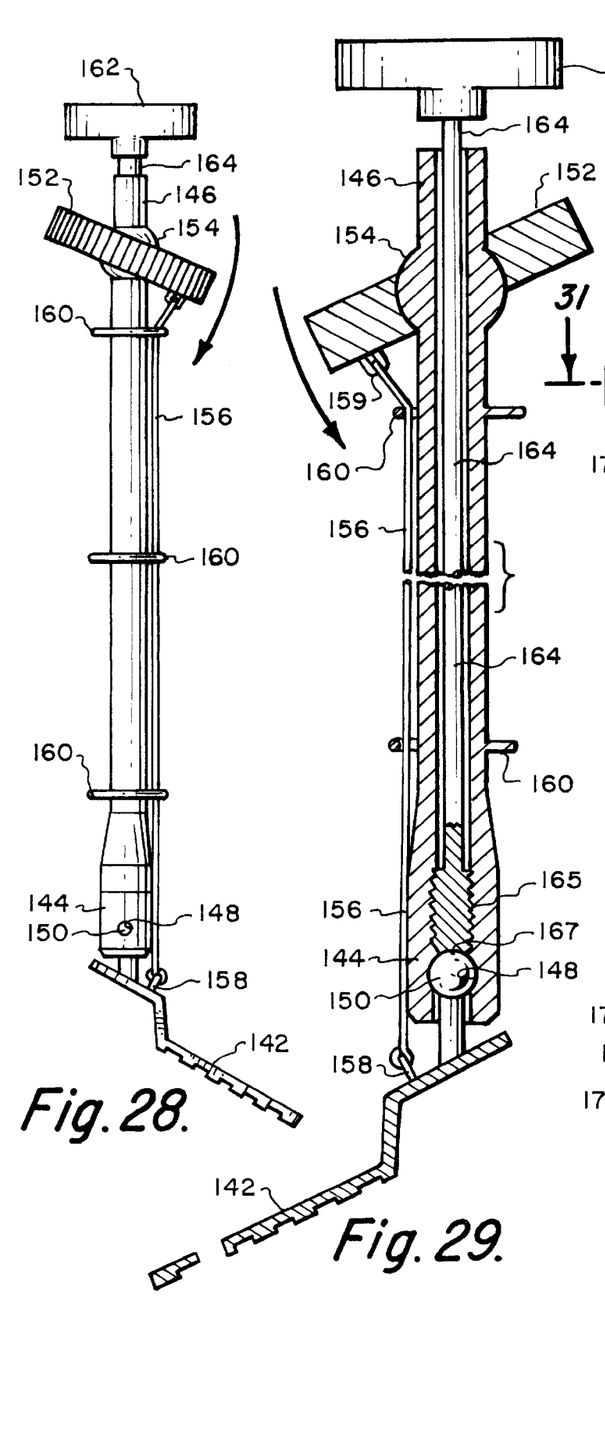
FIG. 28 is a side elevation of the heart stabilizing device of FIG. 25 illustrating adjustment of the flat rectangular stabilizing plate.
FIG. 29 is a sectional view taken at 29—29 of FIG. 27.
Figure 30:
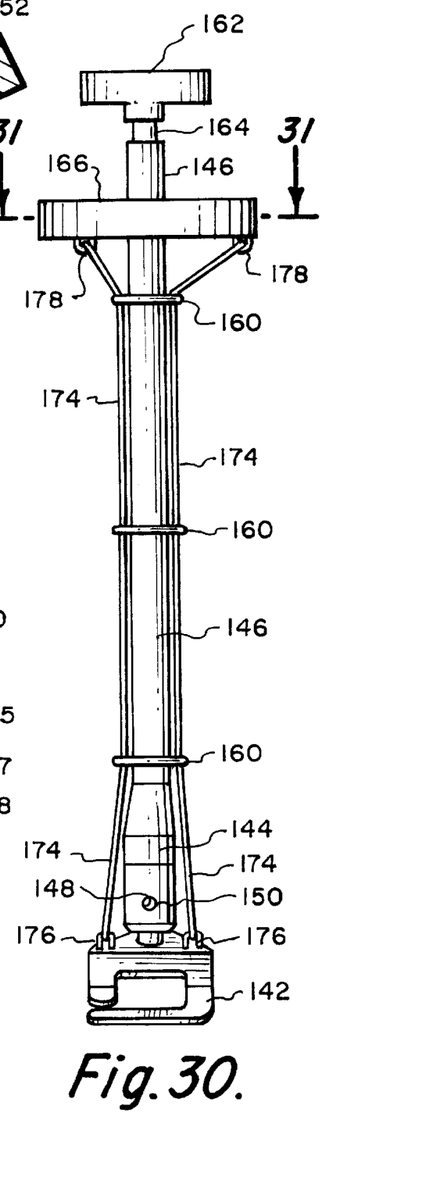
FIG. 30 is a front elevation of yet another embodiment of a heart stabilizing device that can be externally adjusted.

The method of using the externally adjustable stabilizing device is illustrated in FIGS. 26 through 29. The stabilizing device is passed through an incision and stabilizing plate 142 positioned near the surface tissue of the heart on the artery that is occluded. The surgeon can then manipulate or adjust the side to side or up and down position of stabilizing plate 142 by tilting wobble plate 152 mounted on stabilizing ball 154 (FIG. 29). To adjust the position of stabilizing plate once it is placed against the surface tissue of the heart, wobble plate 152 is tilted forward, backward or side to side, or any angle around the circumference of spherical ball 154 which adjusts stabilizing plate accordingly. Wobble plate 152 pulls on lanyards or cables 156 to tilt the stabilizing plate 142 up or down or side to side. Once the stabilizing plate 142 is properly positioned, it is locked in place by rotating handle 162 forcing rod 164 against ball 150 securely clamping the stabilizing plate in the adjusted position. With the device shown in FIGS. 25 through 29, stabilizing plate 142 can be manipulated and adjusted externally through a small incision.

An optional embodiment in which wobble plate 152 is replaced by a gimbal-type arrangement of concentric yokes is illustrated in FIGS. 30 through 34. In this embodiment stabilizing plate 142 is connected to barrel end 144 on shaft 46 with ball 150 seated in socket 148 as before. However, flat rectangular frame or plate 142 is adjusted by means of concentric yoke 166 and 168 mounted on shaft 146 as shown in the sectional views of FIGS. 32 and 34. Circular yoke 168 is attached to rigid shaft 146 by pins 170 perpendicular to the axis of shaft 146. Outer yoke 166 is attached to both inner concentric yoke 168 and shaft 146 by similar pins 172 perpendicular to the axis of shaft 146. Inner mounting pins 170 are at right angles to outer yoke 166 mounting pins 172. This allows outer yoke 166 to move independent of inner yoke 168 around the axis of pins 172 and in conjunction with yoke 166 around the axis of inner yoke mounting pins 170.

Outer yoke 166 is connected to flat rectangular plate 142 by three lanyards 174 connected between annulets 176 and 177 attached to either side and the rear of flat rectangular frame or plate 142 and to outer yoke 166 by annulets 178 and 179. Cable or lanyards 174 are restrained by rings 160 around shaft 146 as before.

Figures 31, 32, 33, 34:
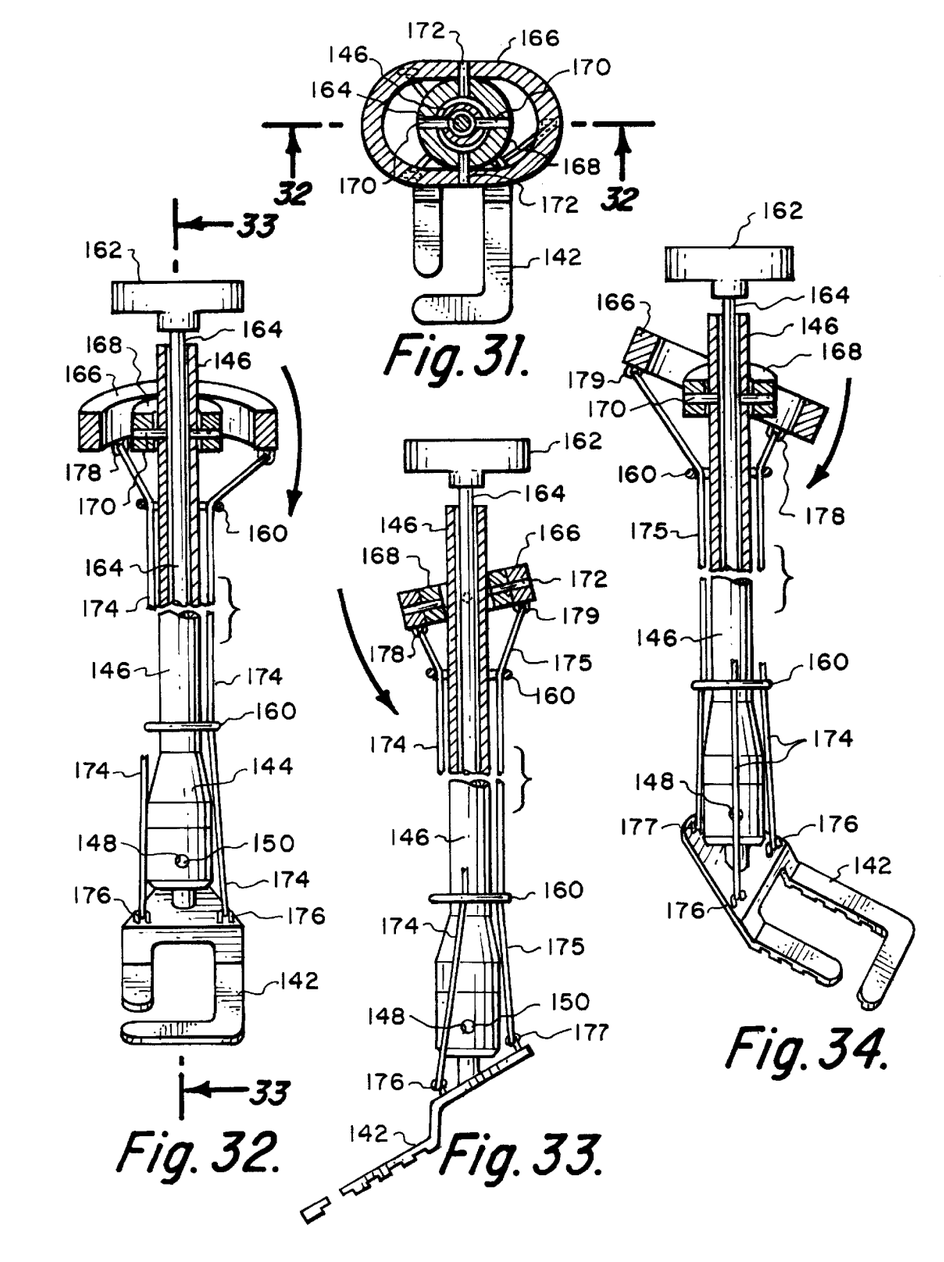
FIG. 31 is a sectional view taken at 31—31 of FIG. 30.
FIG. 32 is a front elevational view of the embodiment of FIG. 30 in partial sections taken at 32—32 of FIG. 31.
FIG. 33 is a partial sectional side elevational view of the heart stabilizing device on FIG. 30 taken at 33—33 of FIG. 32.
FIG. 34 is a partial sectional side elevational view from a side opposite to FIG. 33 illustrating external manipulation and adjustment of the stabilizing plate.

As can be seen by reference to FIGS. 32 through 34 side to side angular adjustment is accomplished by tilting outer yoke 166 from side to side operating cables 174 connected to annulets 176 on plate 142 adjusting the side to side angle of the flat rectangular plate. Front to back angular adjustment is accomplished by rotating outer yoke 166 simultaneously with inner yoke 168 which moves cable 175 connected between eyelet 177 and 179 on the rear of flat rectangular frame 142 and outer yoke 166 respectively. Thus angular adjustment of outer yoke 166 around the axis of mounting pins 170 tilts rectangular frame 142 from front to rear. Simultaneous adjustment of side to side adjustments as well as front to back adjustments can thus adjust flat rectangular frame 142 to any convenient angular position to fit the contour of the heart tissue at the occluded artery where surgery is to be performed.

The embodiment shown in FIGS. 25 through 34 thus allow external adjustment of the heart stabilizing device without the need for the surgeon reaching inside the incision made to perform the operation. In the first embodiment wobble plate 152 can be adjusted to a variety of angular positions to adjust the forward, backward, side to side or any angular position in between. The movement of wobble plate 152 results in corresponding angular movement of flat rectangular frame 142. Likewise in the embodiments of FIGS. 30 through 34 a concentric yoke configuration allows angular movement of outer oval-shaped concentric yoke 166 which results in side to side movement of flat rectangular plate 142 while front to back movement of both inner concentric yoke 168 and outer concentric yoke 166 results in front to back movement of flat rectangular plate 142. Simultaneous front to back and side to side adjustments of both outer concentric yoke 166 and inner concentric yoke 168 above the axis of pins 170 and 172 results in equivalent angular adjustment of flat rectangular frame 142.

Thus either one of the devices shown in these figures can be placed through an incision against the surface tissue of heart where the occluded artery and externally adjusted by movement of the wobble plate 152 or concentric yoke 166 and 168 to conform to the contour of the heart at the surgical site.

The adjusted angular position of flat rectangular frame is then locked in place by tightening down handle 162 tightening rod 164 against ball 150 attached to rectangular frame 142 as shown in FIG. 29. The interior end of rod 164 has a threaded portion 165 and a concave end 167 that matches the contour of ball 150 in socket 148. Once flat rectangular frame has been properly positioned against the heart tissue rotation of handle 162 forces concave end 167 against ball 150 by means of threads 165 to securely lock the frame in the selected angular position.

The use of any one of the flat plate rectangular stabilizer for a anastomosis procedure is illustrated in FIG. 1. Rectangular flat plate stabilizer 12 is placed firmly in position on surface tissue of heart 35 with ends 32 and 34 pressing on vessel 28 to substantially occlude the blood flow. An incision 30 can then be made in the vessel for attachment to a graft to bypass an obstruction. Stabilizer 12 firmly holds surface tissue on heart 35 in the area of vessel 28 against movement from the beating heart. This allows the surgeon to complete the anastomosis without the necessity of connecting the patient to a cardiopulmonary machine. When the graft is successfully and firmly attached to incision 30 in vessel 28, stabilizer 12 may be removed with grafted vessel passing through opening 14.

Thus there has been disclosed a plurality of unique configurations for improved stabilizers for use in stabilizing the heart during heart bypass surgery or anastomosis. The stabilizer allows a surgeon to firmly hold a small surface area of the heart stationery against the motion of the beating heart while surgical grafts can be performed. Stabilizing can be in the form of a rectangular flat plate having a gripping bottom surface and an upper surface configured for attachment to a rigid shaft for adjustment to a various number of angles and positions to perform surgical procedures on all areas of the heart. Optional embodiments include a rectangular frame flat plate stabilizer having a hinged end that can be closed during the surgical procedure to press on end vessel on opposite sides of the surgical site and then opened to allow the stabilizer to be removed. Other features include a cylindrical rail attached to the stabilizer to allow adjustments to a wide variety of positions and angles. In one embodiment the rail is connected only at one end to allow the rail to pass freely through a bore in the rigid shaft to provide a wide range of vertical as well as angular adjustments. In other embodiments the flat rectangular stabilizer is connected to the rigid shaft by a ball and socket arrangement or in another case of a half ball having a clamping cavity receiving a convex tip of a clamping pin.

Obviously many modifications of the invention is possible in light of the above features. It is therefore understood that the full scope of the invention is not limited to the details disclosed herein and may be practiced otherwise then as specifically described.

What is claim is:

1. A heart stabilizing device for stabilizing surface tissue of a heart during heart bypass surgery comprising;
    a flat rectangular frame having an opening along one side for pressing on and stabilizing a small area of surface tissue of said heart where an anastomosis is to be performed;
    a rail mounted on an upper surface of said flat rectangular frame;
    a holder for holding said flat rectangular frame in position on said small area of surface tissue, said holder comprising a rigid shaft removably attached to said rail on said flat rectangular frame having a socket in one end, said rail being seated in said socket;
    said flat rectangular frame being adjusted by moving said rail in said socket on said rigid shaft so that said flat rectangular frame conforms to the center of a small area of surface tissue where the stabilizer is placed; and
    a locking device for locking said flat rectangular frame in an adjusted position;
    whereby both angle and position of said flat rectangular frame may be adjusted for optimal pressure on an area of heart tissue and then locked in that position.

2. The device according to claim 1 in which said flat rectangular frame has a bottom surface formed to improve gripping force on said surface tissue.

3. The device according to claim 2 in which said bottom surface has a plurality of grooves.

4. The device according to claim 2 in which said bottom surface is cross cut to form a plurality of gripping ridges.

5. The device according to claim 2 in which said bottom surface is formed with a plurality of dimples to form an uneven gripping surface.

6. The device according to claim 2 in which said bottom surface is cut to produce a pattern of ridges and grooves forming a tread.

7. The device according to claim 2 including a resilient material attached to said bottom surface to form a capsule; said capsule being filled with a pliant material.

8. The device according to claim 7 in which said pliant material is a gel.

9. A heart stabilizing device for stabilizing surface tissue of a heart during heart bypass surgery comprising;
    a flat rectangular frame having an opening along one side for pressing on and stabilizing a small area of surface tissue of said heart where an anastomosis is to be performed;
    a holder for holding said flat rectangular frame in position on said small area of surface tissue, said holder comprising a rigid shaft removably attached to said flat rectangular frame,
    a half-spherical ball having a central cavity attached to a flange on said flat rectangular frame, said ball constructed to fit in a socket in an end of said rigid shaft;

said flat rectangular frame being adjusted by moving said half-spherical ball in said socket on said rigid shaft so that said flat rectangular frame conforms to shape and angle of a small area of surface tissue where the stabilizer is to be placed;

a locking device in said shaft for locking said flat rectangular frame in an adjusted position, said locking device comprising a rod inside said rigid shaft having an end constructed to fit inside said central cavity in said half-spherical ball and a clamp for clamping said rod with said end firmly pressed in said socket in said half-spherical ball;

whereby both angle and position of said flat rectangular frame may be adjusted for optimal pressure on an area of heart tissue and then locked in that position.

10. A heart stabilizing device for stabilizing surface tissue of a heart during heart bypass surgery comprising;

a flat rectangular frame having an opening along one side for pressing on and stabilizing a small area of surface tissue of said heart where an anastomosis is to be performed, said opening along one side of said flat rectangular frame being a hinged section whereby said hinged section is adapted to open and close for removal of said stabilizer after completing an anastomosis;

a holder for holding said flat rectangular frame in position on said small area of tissue, said holder allowing adjustment of both position and angle of said flat rectangular frame to conform to the center of the small area of surface tissue where the stabilizer is placed.

11. A heart stabilizing device for stabilizing surface tissue of a heart during heart bypass surgery comprising;

a flat rectangular frame having an opening along one side for pressing on and stabilizing a small area of surface tissue of said heart where an anastomosis is to be performed;

a rigid shaft attached to said flat rectangular frame for holding said flat rectangular frame in position on said small area of tissue;

said flat rectangular plate being movably attached to said rigid shaft by a rod passing through said rigid shaft;

a connector for connecting said flat rectangular frame to said rod passing through said rigid shaft, said connector comprising;

a boss attached to a flange on said flat rectangular frame, a dowel inserted in a hole in said boss, a screw constructed for insertion through a slot in said boss into a threaded hole in said dowel, said screw passing through an eyelet on an end of said rod, said screw and boss having mutually opposing angled surfaces for engaging an end of said rigid shaft for locking the position of said stabilizer;

a locking device for locking aid flat rectangular plate against an end of said rigid shaft, said locking device comprising a handle threaded on an upper end of said rod for tightening said mutually opposing angled surfaces against an end of said rigid shaft;

whereby both angle and position of said flat rectangular frame may be adjusted for optimal pressure on an area of heart tissue and then locked in that position.

12. The device according to claim 11 in which said mutually opposing angled surfaces comprises conical surfaces on a head on said screw and on a side of said boss.

13. A heart stabilizing device for stabilizing surface tissue of a heart during heart bypass surgery comprising;

a flat rectangular frame having an opening along one side for pressing on and stabilizing a small area of surface tissue of said heart where an anastomosis is to be performed;

a holder for holding said flat rectangular frame in position on said small area of tissue, said holder including a rigid shaft attached to said flat rectangular frame;

an adjustable attachment for adjustably attaching said flat rectangular frame to said rigid shaft, said adjustable attachment comprising;

a ball on a flange attached to said flat rectangular frame, a socket on an end of said rigid shaft for receiving said ball;

remote adjustment device for remotely adjusting said flat rectangular frame on said rigid shaft, said remote adjustment device comprising;

at least one angularly adjustable ring on an end of said rigid shaft remote from said flat rectangular frame, joining means for joining said at least on angularly adjustable ring for angular movement around a first and second axis for angular adjustment of said flat rectangular frame;

a locking device for locking said flat rectangular frame after angular adjustment, said locking device comprising;

a rod inside a bore in said rigid shaft, a handle for tightening said rod against said ball on said flat rectangular plate;

whereby said flat rectangular plate may be adjustably positioned against an area of heart tissue and locked in the adjusted position.

14. A heart stabilizing device according to claim 13 wherein said at least one angularly adjustable ring comprises a wobble plate mounted on a ball formed on an end of said rigid shaft remote from said flat rectangular plate.

15. The device according to claim 14 in which said connecting means comprises cable means connecting said flat rectangular plate to said concentric yokes whereby angular adjustment of said concentric yokes produces nearly identical angular adjustment of said flat rectangular plate so that said flat rectangular plate can be adjusted to the contour of the surface of the heart externally.

16. The device according to claim 15 including means for locking said flat rectangular plate at an adjusted angular position.

17. The device according to claim 16 in which said locking means comprises; a rod in said rigid shaft; and clamp means for clamping an in inner end of said rod against said ball mounted on said flat rectangular frame.

18. A heart stabilizing device according to claim 13 wherein said at least one angularly adjustable ring comprises a pair of concentric angularly movable yokes on a remote end of said rigid shaft.

* * * * *

UNITED STATES PATENT AND TRADEMARK OFFICE
CERTIFICATE OF CORRECTION

PATENT NO. : 6,113,534
DATED : September 5, 2000
INVENTOR(S) : Tibor B. Koros and Gabriel J. Koros It is certified that error appears in the above-identified patent and that said Letters Patent are hereby corrected as shown below:

```
Column 2,  line 15,  delete "e" and insert -- the --;
Claim 1,   line 31,  delete "stabilizer" and insert
                     -- frame --;
Claim 9,   line 5,   delete "stabilizer" and insert
                     -- frame --;
Claim 10,  line 24,  delete "stabilizer" and insert
                     -- frame --;
Claim 11,  line 55,  delete "stabilizer" and insert
                     -- frame --;
           line 56,  delete "aid" and insert -- said --;
Claim 13,  line 26,  delete "on" and insert -- one --.
```

Signed and Sealed this

First Day of May, 2001

Attest:

NICHOLAS P. GODICI

Attesting Officer     Acting Director of the United States Patent and Trademark Office